United States Patent
Alchas (10) Patent No.: US 9,750,897 B2
(45) Date of Patent: Sep. 5, 2017

(54) INTRADERMAL DELIVERY DEVICE INCLUDING A NEEDLE ASSEMBLY

(71) Applicant: Becton, Dickinson and Company, Franklin Lakes, NJ (US)

(72) Inventor: Paul G. Alchas, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/576,347

(22) Filed: Dec. 19, 2014

(65) Prior Publication Data
US 2015/0231338 A1    Aug. 20, 2015

Related U.S. Application Data

(60) Continuation of application No. 14/081,412, filed on Nov. 15, 2013, now abandoned, which is a continuation of application No. 11/871,012, filed on Oct. 11, 2007, now abandoned, which is a continuation of application No. 09/825,017, filed on
(Continued)

(51) Int. Cl.
| | |
|---|---|
| *A61M 5/46* | (2006.01) |
| *A61M 37/00* | (2006.01) |
| *A61M 5/28* | (2006.01) |
| *A61D 7/00* | (2006.01) |
| *A61M 5/32* | (2006.01) |

(52) U.S. Cl.
CPC .............. *A61M 5/46* (2013.01); *A61M 37/00* (2013.01); *A61D 7/00* (2013.01); *A61M 5/282* (2013.01); *A61M 5/3202* (2013.01); *A61M 5/3278* (2013.01); *A61M 2202/0445* (2013.01)

(58) Field of Classification Search
CPC .............. A61M 5/3202; A61M 5/3213; A61M 5/3216; A61M 5/3243; A61M 5/326; A61M 5/46; A61M 5/32
USPC ... 604/117, 192, 82–92, 187, 199, 235, 200, 604/198, 171, 197
See application file for complete search history.

(56) References Cited

U.S. PATENT DOCUMENTS

| 1,274,081 A | 7/1918 | Riethmueller | |
|---|---|---|---|
| 1,453,309 A * | 5/1923 | Eberly, Jr. ............... | A61M 5/46 604/117 |

(Continued)

FOREIGN PATENT DOCUMENTS

| DE | 4127887 C1 | 1/1993 |
|---|---|---|
| EP | 0279583 B1 | 2/1988 |

(Continued)

OTHER PUBLICATIONS

Article: Dermal Immune System by Brian J. Nickoloff, MD, PhD.
(Continued)

*Primary Examiner* — Manuel Mendez
(74) *Attorney, Agent, or Firm* — The Webb Law Firm (57) ABSTRACT

A drug delivery device including a needle assembly facilitates making intradermal injections using a variety of drug container types such as a syringe. A hub supports the needle while a limiter surrounds the needle. The limiter includes a skin engaging surface that is adapted to be received against the skin of an animal to be intradermally injected. A forward end of the needle extends beyond the skin engaging surface a selected distance to limit a depth that the needle penetrates into the animal's skin.

10 Claims, 5 Drawing Sheets

Related U.S. Application Data

Apr. 3, 2001, now abandoned, which is a division of application No. 09/417,671, filed on Oct. 14, 1999, now Pat. No. 6,494,865.

(56) References Cited

U.S. PATENT DOCUMENTS

| | | | |
|---|---|---|---|
| 1,934,046 A | 11/1933 | Demarchi | |
| 2,559,474 A | 7/1951 | Son | |
| 2,876,770 A | 3/1959 | White | |
| 3,179,107 A * | 4/1965 | Clark | A61M 5/348 604/242 |
| 3,400,715 A | 9/1968 | Pederson | |
| 3,406,687 A * | 10/1968 | Moyer | A61M 5/3243 604/117 |
| 3,737,973 A * | 6/1973 | Stawski | A61M 5/31551 29/235 |
| 3,934,590 A * | 1/1976 | Campagna | A61F 9/0026 604/302 |
| 4,060,073 A | 11/1977 | Collicá et al. | |
| 4,270,537 A | 6/1981 | Romaine | |
| 4,373,526 A * | 2/1983 | Kling | A61M 5/46 604/117 |
| 4,481,001 A | 11/1984 | Graham et al. | |
| 4,583,978 A | 4/1986 | Porat et al. | |
| 4,596,556 A | 6/1986 | Morrow et al. | |
| 4,718,463 A | 1/1988 | Jurgens, Jr. et al. | |
| 4,769,003 A | 9/1988 | Stamler | |
| 4,778,453 A * | 10/1988 | Lopez | A61M 5/3202 604/110 |
| 4,790,824 A | 12/1988 | Morrow et al. | |
| 4,816,024 A * | 3/1989 | Sitar | A61M 5/3243 604/192 |
| 4,883,473 A | 11/1989 | Thomas | |
| 4,883,573 A | 11/1989 | Voss et al. | |
| 4,886,499 A | 12/1989 | Cirelli et al. | |
| 4,898,588 A | 2/1990 | Roberts | |
| 4,940,460 A | 7/1990 | Casey, I. et al. | |
| 4,941,880 A | 7/1990 | Burns | |
| 4,955,871 A * | 9/1990 | Thomas | A61M 5/282 222/107 |
| 4,978,344 A | 12/1990 | Dombrowski et al. | |
| 5,015,235 A | 5/1991 | Crossman | |
| 5,064,413 A | 11/1991 | McKinnon et al. | |
| 5,071,353 A | 12/1991 | van der Wal | |
| 5,141,496 A | 8/1992 | Dalto et al. | |
| 5,190,521 A | 3/1993 | Hubbard et al. | |
| 5,207,983 A | 5/1993 | Liebert et al. | |
| 5,222,949 A | 6/1993 | Kaldany | |
| 5,241,969 A | 9/1993 | Carson et al. | |
| 5,248,300 A * | 9/1993 | Bryant | A61M 5/14244 128/DIG. 12 |
| 5,256,154 A | 10/1993 | Liebert et al. | |
| 5,312,335 A | 5/1994 | McKinnon et al. | |
| 5,328,483 A | 7/1994 | Jacoby | |
| 5,331,954 A | 7/1994 | Rex et al. | |
| 5,334,144 A | 8/1994 | Alchas et al. | |
| 5,339,163 A | 8/1994 | Homma et al. | |
| 5,364,387 A * | 11/1994 | Sweeney | A61J 1/2096 604/239 |
| 5,368,578 A | 11/1994 | Covington et al. | |
| 5,373,684 A | 12/1994 | Vacca | |
| 5,383,851 A | 1/1995 | McKinnon, Jr. et al. | |
| 5,417,662 A | 5/1995 | Hjertman et al. | |
| 5,431,155 A | 7/1995 | Marelli | |
| 5,437,647 A | 8/1995 | Firth et al. | |
| 5,466,220 A | 11/1995 | Brenneman | |
| 5,496,286 A | 3/1996 | Stiehl et al. | |
| 5,503,627 A | 4/1996 | McKinnon et al. | |
| 5,505,694 A * | 4/1996 | Hubbard | A61M 5/282 604/242 |
| 5,514,107 A | 5/1996 | Haber et al. | |
| 5,519,984 A | 5/1996 | Beussink et al. | |
| 5,520,639 A | 5/1996 | Peterson et al. | |
| 5,527,288 A | 6/1996 | Gross et al. | |
| 5,531,255 A | 7/1996 | Vacca | |
| 5,569,089 A | 10/1996 | Signorelli | |
| 5,573,042 A | 11/1996 | De Haen | |
| 5,578,014 A | 11/1996 | Erez et al. | |
| 5,582,598 A | 12/1996 | Chanoch | |
| 5,597,530 A | 1/1997 | Smith et al. | |
| 5,599,302 A | 2/1997 | Lilley et al. | |
| 5,620,425 A | 4/1997 | Heffernan et al. | |
| 5,649,912 A | 7/1997 | Peterson | |
| 5,665,071 A | 9/1997 | Wyrick | |
| 5,702,362 A | 12/1997 | Herold et al. | |
| 5,704,911 A | 1/1998 | Parsons | |
| 5,779,677 A | 7/1998 | Frezza | |
| 5,848,991 A * | 12/1998 | Gross | A61M 5/14248 604/140 |
| 5,873,856 A | 2/1999 | Hjertman et al. | |
| 5,879,327 A | 3/1999 | Moreau DeFarges et al. | |
| 5,891,085 A | 4/1999 | Lilley et al. | |
| 5,893,397 A | 4/1999 | Peterson et al. | |
| 5,921,963 A | 7/1999 | Erez et al. | |
| 5,957,897 A | 9/1999 | Jeffrey | |
| 5,961,495 A | 10/1999 | Walters et al. | |
| 5,993,412 A | 11/1999 | Deily et al. | |
| 6,001,089 A | 12/1999 | Burroughs et al. | |
| 6,004,299 A | 12/1999 | Arai et al. | |
| 6,007,529 A * | 12/1999 | Gustafsson | A61J 1/00 206/219 |
| 6,036,675 A | 3/2000 | Thorne et al. | |
| 6,053,893 A | 4/2000 | Bucher | |
| 6,083,197 A | 7/2000 | Umbaugh | |
| 6,090,077 A | 7/2000 | Shaw | |
| 6,090,080 A | 7/2000 | Jost et al. | |
| 6,090,082 A | 7/2000 | King et al. | |
| 6,093,170 A | 7/2000 | Hsu et al. | |
| 6,112,743 A | 9/2000 | Denton | |
| 6,183,489 B1 * | 2/2001 | Douglas | A61B 5/1411 600/583 |
| 6,200,291 B1 | 3/2001 | Di Pietro | |
| 6,319,230 B1 | 11/2001 | Palasis et al. | |
| 6,332,875 B2 * | 12/2001 | Inkpen | 604/117 |
| 6,494,865 B1 | 12/2002 | Alchas | |
| 6,503,231 B1 | 1/2003 | Prausnitz et al. | |
| 6,525,030 B1 | 2/2003 | Eriksson | |
| 6,562,002 B1 * | 5/2003 | Taylor | A61M 5/282 604/82 |
| 6,623,457 B1 | 9/2003 | Rosenberg | |
| 6,808,506 B2 | 10/2004 | Lastovich et al. | |

FOREIGN PATENT DOCUMENTS

| | | |
|---|---|---|
| EP | 0904790 A2 | 3/1999 |
| FR | 2612401 A1 | 9/1988 |
| GB | 2206794 A | 1/1989 |
| JP | 2000037456 A | 2/2000 |
| WO | 9423777 A1 | 10/1994 |
| WO | 9501198 A1 | 1/1995 |
| WO | 9713537 A1 | 4/1997 |
| WO | 9737705 A1 | 10/1997 |
| WO | 9927986 A1 | 6/1999 |
| WO | 9934850 A1 | 7/1999 |

OTHER PUBLICATIONS

Article: Trials of Intradermal Hepatitis B Vaccines in Gambian Children by Whittle, Lamb, Ryder.

Article: Injection of Technique Intradermal.

Article: The Dendritic Cell System and Its Role in Immunogenicity by Ralph Steinman.

Article: Intradermal Gene Immunization: The Possible Role of DNA Uptake in the Induction of Cellular Immunity to Viruses by: Eyal Raz et al.

Article: Clinical Do's & Dont's—Giving Intradermal Injections by Edwina McConnell, RN, Ph.D.

Article: Monographs of the Physiological Society No. 12: Substances Producing Pain and Itch by C.A. Keele and D. Armstrong, Pub: The Williams & Wilkins Company (1964).

(56) References Cited

OTHER PUBLICATIONS

Phillips, et al., Purified Influenza Vaccine: Clinical and Serologic Response to Varying Doses and Different Routes of Immunization, Department of Medicine and Community Medicine, Univiversity of Vermont College of Medicine, Burlington, Vermont.

Clark et al., Polyvalent Influenza Vaccine: Comparison of Jet Injection with Intradermal and Subcutaneous Syringe Methods of Administration, Oklahoma City, Oklahoma.

"Experimental Comparison of Intradermal and Subcutaneous Vaccination with Influenza Vaccine", Amer. J. of Med. Tech., (Nov.-Dec. 1965), vol. 31, No. 6.

"Intradermal Influenza Immunization, Experience with Hong Kong Vaccine", American Review of Respiratory Disease, (1971), vol. 103.

Niculescu et al., "Efficacy of Adsorbed Trivalent Split Influenza Vaccine Administered by Intradermal Route", received for publication Dec. 4, 1980, from Arch. Roum. Path. Exp. Microbiol., T. 40, No. 1, pp. 67-70, Janvier-Mars. 1981).

"Efficacy of Intradermally Administered A2 Hong Kong Vaccine", from JAMA, (Jul. 6, 1970), vol. 213, No. 1.

Herbert et al., "Comparison of Responses to Influenza, A-New Jersey/76-A/Victoria/75 Virus Vaccine Administered Intradermally or Subcutaneously to Adults with Chronic Respiratory Disease", J. of Infectious Diseases, (Aug. 1979), vol. 10, No. 2.

Halperin et al., "A Comparison of the Intradermal and Subcutaneous Routes of Influenza Vaccination with A/New Jersey/76 (Swine Flu) and A/Victoria/75: Report of a Study and Review of the Literature", Alpha, (Dec. 1979), vol. 69, No. 12.

"Effect of Dosage and Route of Inoculation Upon Antigenicity of Inactivated Influenza Virus Vaccine (Hong Kong Strain) in Man", from Bull. Org. mond. SantéBull. Wld Hlth Org., (1969), vol. 41, pp. 507-516.

"Comparative Analysis of Six European Influenza Vaccines", Eur. J. Clin. Microbiol. Infect. Dis., (1996), vol. 15, pp. 121-127.

Renfry et al., "Morphological and Biochemical Characterization of Influenza Vaccines Commercially Available in the United Kingdom", Vaccine, (1994), vol. 12, No. 8.

"Influenza Immunization Policies and Practices in Japan", Journal of Infectious Diseases, (Feb. 1980), vol. 141, No. 2.

Parent Du Chatelet, et al., "Clinical Immunogenicity and Tolerance Studies of Liquid Vaccines Delivered by Jet-Injector and a New Single-Use Cartridge (Imule® Comparison) with Standard Syringe Injection", Vaccine, (1997), vol. 15, No. 4.

Polillio et al., "Does a Needleless Injection System Reduce Anxiety in Children Receiving Intramuscular Injections?", Pediatric Primary Care Clinic, Boston City Hospital, MA, USA, Pediatr. Nurs., (Jan.-Feb. 1997), vol. 23, No. 1, pp. 46-49. (Abstract).

Nagafuchi et al., "Intradermal Administration of Viral Vaccines", Rev. Med. Virol., (Apr. 1998), vol. 8, No. 2, pp. 97-111. (Abstract).

Payler et al., "Letter: Intradermal Influenza Vaccination", Br. Med. J., (Jun. 29, 1974), vol. 2, No. 921, p. 727. (Abstract).

"Intradermal Influenza Vaccination", British Medical Journal, (Jun. 29, 2974).

Smith Kline Beecham Meeting Agenda.

\* cited by examiner

INTRADERMAL DELIVERY DEVICE INCLUDING A NEEDLE ASSEMBLY

CROSS-REFERENCE TO RELATED APPLICATIONS

This application is a continuation of Ser. No. 14/081,412 which is a continuation of Ser. No. 11/871,012, filed Oct. 11, 2007, now abandoned, which is a continuation of Ser. No. 09/825,017, filed Apr. 3, 2001, now abandoned, which is a divisional application of Ser. No. 09/417,671 filed Oct. 14, 1999, now patented as U.S. Pat. No. 6,494,865.

FIELD OF THE INVENTION

The present invention generally relates to delivery devices for delivering substances such as drugs, vaccines and the like, and more specifically relates to a drug delivery device for injecting such substances intradermally, i.e., into the skin. In addition, the present invention relates to a needle assembly that is adaptable for use with a variety of drug containers such as syringes for making intradermal injections.

BACKGROUND OF THE INVENTION

A wide variety of hypodermic injection devices are commercially available. Most hypodermic injections are intended to be intramuscular so that the hypodermic needle penetrates through an individual's skin layer and subcutaneous tissue and into the muscle tissue. Under some circumstances, however, limited needle penetration is desired. Under some circumstances, for example, an intradermal injection is desired where the needle does not penetrate beyond the dermis layer.

One technique for administering intradermal injections is known as the Mantoux procedure. A Mantoux procedure is relatively complicated and requires technical skill from the medical professional or individual administering the injection. Additionally, the Mantoux procedure can prove painful for the individual receiving the injection, especially when somebody without experience is administering the injection.

Devices have been proposed for providing intradermal injections, which include shortened needles compared to conventional needle sizes. The smaller needles are not intended to penetrate beyond the dermis layer of the individual. Such devices are shown in U.S. Pat. No. 5,527,288, which issued on Jun. 18, 1996; U.S. Pat. No. 4,886,499, which issued on Dec. 12, 1989; and U.S. Pat. No. 5,328,483, which issued on Jul. 12, 1994. The proposed devices, however are not without shortcomings and drawbacks.

For example, the devices shown in U.S. Pat. Nos. 5,527,288 and 4,886,499 are highly specialized injectors. The designs for these injectors include relatively complex arrangements of components that cannot be economically manufactured on a mass production scale. Therefore, such devices have limited applicability and use.

Similarly, the device shown in U.S. Pat. No. 5,328,483 requires a specially designed injector and, therefore, it is not readily adapted to be used with a variety of syringe types. Additionally, the assembly of that patent is not conducive to economical mass production.

There is need for an intradermal injection device that is suitable for use with a variety of syringe bodies. Additionally, there is a need for an intradermal injection device that can be economically manufactured on a mass production scale. This invention addresses those needs and avoids the shortcomings and drawbacks discussed above.

SUMMARY OF THE INVENTION

In contrast to the prior devices discussed above, it has been found that a drug delivery device particularly suited for use in intradermally injecting substances such as drugs, vaccines and the like can be constructed in accordance with the present invention. Specifically, the present invention is directed to a drug delivery device including a needle assembly for use in making intradermal injections. The needle assembly has an adapter that is attachable to prefillable containers such as syringes and the like. The needle assembly is supported by the adapter and has a hollow body with a forward end extending away from the adapter. A limiter surrounds the needle and extends away from the adapter toward the forward end of the needle. The limiter has a skin engaging surface that is adapted to be received against the skin of an animal such as a human. The needle forward end extends away from the skin engaging surface a selected distance such that the limiter limits the amount or depth that the needle is able to penetrate through the skin of an animal.

In addition, the present invention is directed to a method of intradermally injecting at least one substance into the skin including the steps of pressing the needle perpendicularly to the skin of the person to receive an injection, injecting the substance into skin of the person with the depth of penetration of the needle being mechanically limited to the intradermal space by the limiter that surrounds the needle. Also, in the preferred embodiment, the step of pressing the needle perpendicularly to the skin of the person includes orienting the needle perpendicularly to the skin, and the step of injecting the substance either includes moving a plunger that is received within the reservoir or deflecting two sheets of thermoplastic material forming the reservoir toward each other to expel the substance from the reservoir during an injection.

The various features and advantages of this invention will become apparent to those skilled in the art from the following detailed description of the currently preferred embodiments. The drawings that accompany the detailed description can be briefly described as follows.

DETAILED DESCRIPTION OF THE PREFERRED EMBODIMENTS

Figure 1:
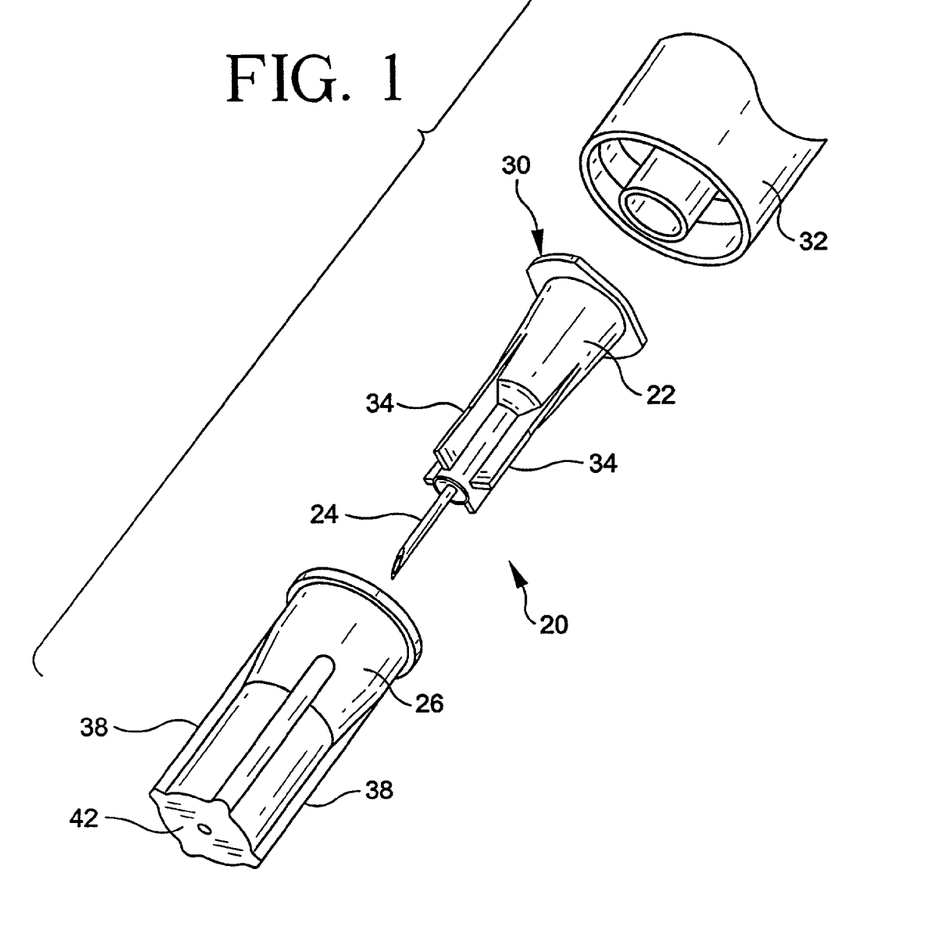
FIG. 1 is an exploded, perspective illustration of a needle assembly designed according to this invention.
Figure 2:
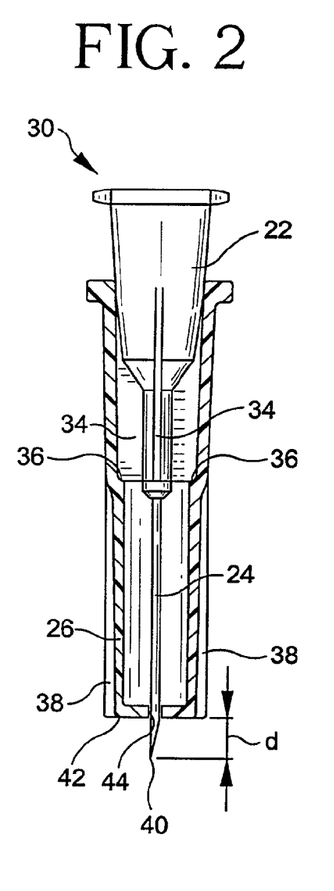
FIG. 2 is a partial cross-sectional illustration of the embodiment of FIG. 1.
Figure 3:
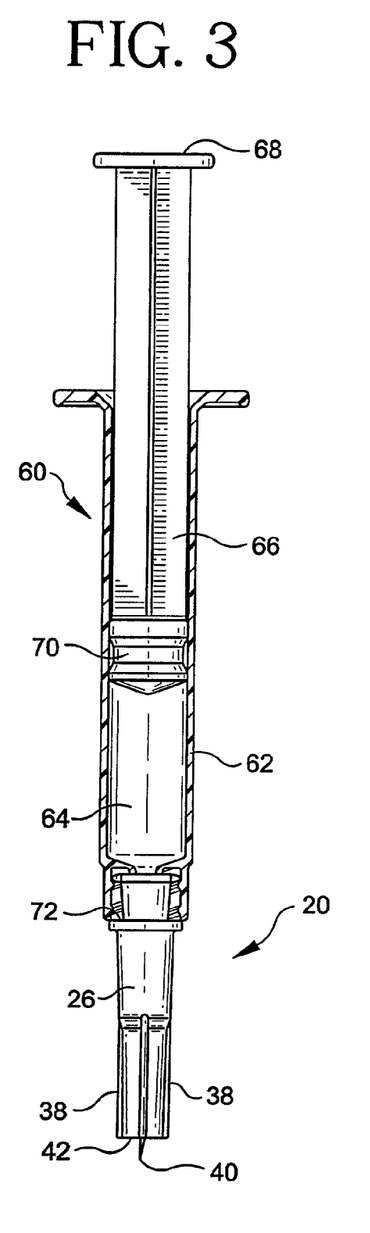
FIG. 3 shows the embodiment of FIG. 2 attached to a syringe body to form an injection device.

FIGS. 1 and 2 diagrammatically illustrate the needle assembly 20 of the present invention that is designed to be used for making intradermal injections, FIG. 3 illustrates the drug container such as syringe 60 for use with the needle assembly 20, and FIGS. 4-7 illustrated the intradermal delivery device 80 of the present invention for making intradermal injections. Intradermal injections include administering substances such as drugs, vaccines and the like into the skin of an animal such as a human.

The needle assembly 20 includes a hub 22 that supports a needle 24. The limiter 26 receives at least a portion of the hub 22 so that the limiter 26 generally surrounds the needle 24 as best seen in FIG. 2.

One end 30 of the hub 22 is able to be secured to a receiver 32 of a syringe. A variety of syringe types can be used with a needle assembly designed according to this invention, with several examples being given below. The opposite end of the hub 22 preferably includes extensions 34 that are nestingly received against abutment surfaces 36 within the limiter 26. A plurality of ribs 38 preferably are provided on the limiter 26 to provide structural integrity and to facilitate handling the needle assembly 20.

By appropriately designing the size of the components, a distance d between a forward end or tip 40 of the needle 24 and a skin engaging surface 42 on the limiter 26 can be tightly controlled. The distance d preferably is in a range from approximately 0.5 millimeters to approximately 3 millimeters. When the forward end 40 of the needle 24 extends beyond the skin engaging surface 42 a distance within that range, an intradermal injection is ensured because the needle is unable to penetrate any further than the typical dermis layer of an animal. Typical tissue layers include an epidermis between 50 and 100 micrometers, a dermis layer between 2 and 3 mm then subcutaneous tissue followed by muscle tissue.

As can be best seen in FIG. 2, the limiter 26 includes an opening 44 through which the forward end 40 of the needle 24 protrudes. The dimensional relationship between the opening 44 and the needle 40 can be controlled depending on the needs of a particular situation. For example, the skin engaging surface 42 surrounding the needle 24 has a thickness defined between an inner diameter and an outer diameter and the inner diameter is at least five times greater than an outside diameter of the needle 24. In the illustrated embodiment, the skin engaging surface 42 is generally planar and continuous and provides a stable placement of the needle assembly 20 against an animal's skin. Although not specifically illustrated, it may be advantageous to have the skin engaging surface be slightly concave or convex in order to facilitate stretching or gathering the animal's skin in the vicinity of the needle tip 40 to facilitate making an injection. Additionally, the ribs 38 may be extended beyond the skin engaging surface 42 to further facilitate manipulating the skin in the vicinity where the injection is to be given.

Regardless of the shape or contour of the skin engaging surface 42, the preferred embodiment includes enough of a surface area that contacts the skin to facilitate stabilizing the injector relative to the animal's skin. In the most preferred arrangement, the skin engaging surface 42 facilitates maintaining the injector in a generally perpendicular orientation relative to the skin surface.

It is important to note that although FIGS. 1 and 2 illustrate a two-piece assembly where the hub 22 is made separate from the limiter 26, this invention is not limited to such an arrangement. Forming the hub 22 and limiter 26 integrally from a single piece of plastic material is an alternative to the example shown in FIGS. 1 and 2. Additionally, it is possible to adhesively or otherwise secure the hub 22 to the limiter 26 in the position illustrated in FIG. 2 so that the needle assembly 20 becomes a single piece unit upon assembly.

Having a hub 22 and limiter 26 provides the advantage of making an intradermal needle practical to manufacture. The preferred needle size is a small gauge hypodermic needle, commonly known as a 30 gauge or 31 gauge needle. Having such a small diameter needle presents a challenge to make a needle short enough to prevent undue penetration beyond the dermis layer of an animal. The limiter 26 and the hub 22 facilitate utilizing a needle 24 that has an overall length that is much greater than the effective length of the needle, which penetrates the individual's tissue during an injection. With a needle assembly designed according to this invention, manufacturing is enhanced because larger length needles can be handled during the manufacturing and assembly processes while still obtaining the advantages of having a short needle for purposes of completing an intradermal injection.

FIG. 3 illustrates a needle assembly 20 secured to a drug container such as a syringe 60. A generally cylindrical syringe body 62 can be made of plastic or glass as is known in the art. The syringe body 62 provides a reservoir 64 for containing a substance to be administered during an injection. A plunger 66 has a manual activation flange 68 at one end with a stopper 70 at an opposite end as known in the art. Manual movement of the plunger 66 through the reservoir 64 forces the substance within the reservoir 64 out of the end 40 of the needle as desired.

The hub 22 can be secured to the syringe body 62 in a variety of known manners. In one example, an interference fit is provided between the interior of the hub 22 and the exterior of the outlet port portion 72 of the syringe body 62. In another example, a conventional luer fit arrangement is provided to secure the hub 22 on the end of the syringe 60. As can be appreciated from FIG. 3, a needle assembly designed according to this invention is readily adaptable to a wide variety of conventional syringe styles.

Figure 4:
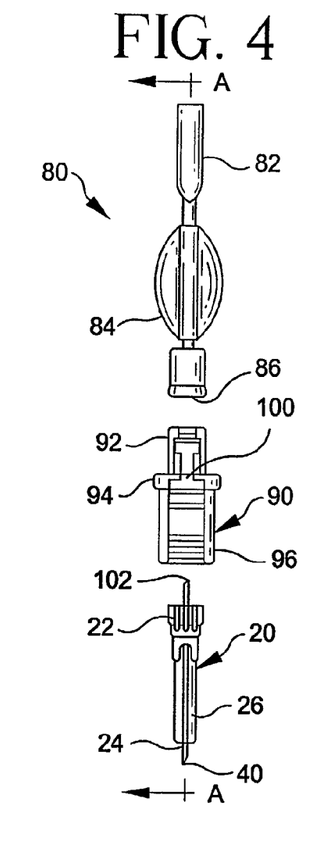
FIG. 4 is an exploded, side view of another embodiment of an injection device designed according to this invention.
Figure 5:
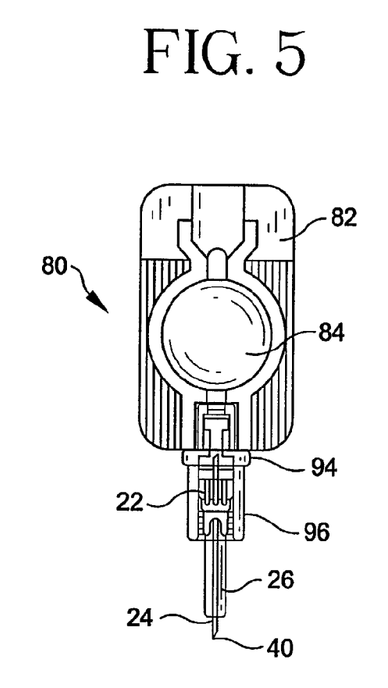
FIG. 5 is a cross-sectional illustration taken along the lines A-A in FIG. 4 but showing the components in an assembled condition.

FIGS. 4 and 5 illustrate an alternative embodiment of an intradermal delivery device 80 that includes a syringe made from two sheets of thermoplastic material. The syringe includes a body portion 82 that is generally flat and surrounds a reservoir 84. An outlet port 86 allows fluid substance within the reservoir 84 to be communicated out of the reservoir to administer an injection. The syringe body preferably is formed using a thermoforming process as is known in the art.

A receiver 90 includes a generally cylindrical neck portion 92 that preferably is secured to the outlet port 86 using a heating or welding process as known in the art. A flange 94 preferably rests against the body portion 82 of the syringe to provide structural integrity. An extension 96 extends away from the flange 94 in a direction opposite from the cylindrical portion 92. The needle assembly 20 preferably is received within the extension 96 as shown in FIG. 5.

The receiver 90 preferably supports a sealing membrane 100 that closes off the outlet port 86 so that the syringe can be prefilled. The needle assembly 20 preferably includes a back end 102 of the needle that penetrates the sealing membrane 100 when the hub 22 is received within the extension 96.

Figure 6:
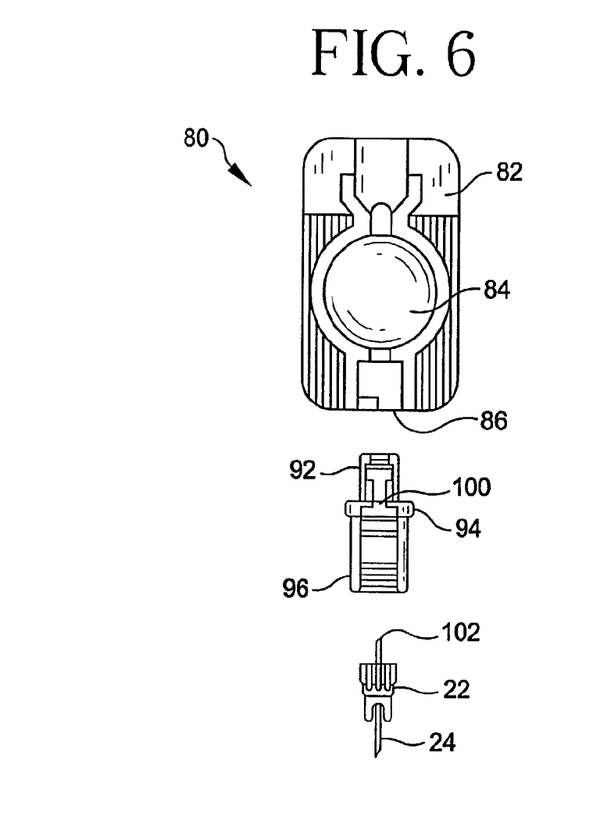
FIG. 6 is an exploded, cross-sectional view similar to that shown in FIG. 5 showing an alternative embodiment.
Figure 7:
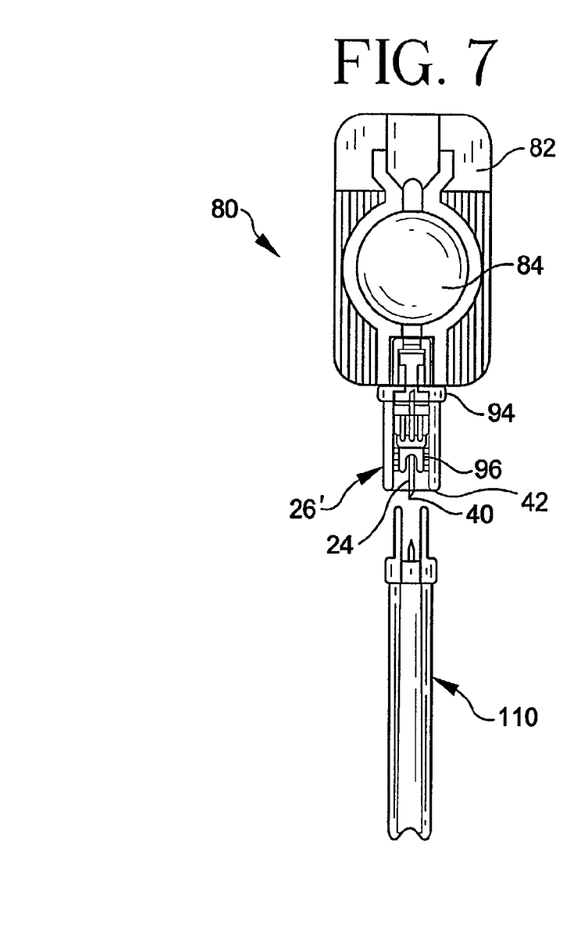
FIG. 7 shows the embodiment of FIG. 6 in an assembled condition.

The side walls of the reservoir 84 preferably are squeezed between a thumb and index finger so that the side walls collapse towards each other and the substance within the reservoir 84 is expelled through the opening in the forward end 40 of the needle 24. In the embodiment of FIGS. 4 and 5, the hub 22 and limiter 26 preferably are integrally molded as a single piece of plastic material. A snap fit arrangement secures the hub 22 within the extension 96 of the receiver 90. Another alternative is illustrated in FIGS. 6 and 7. In this embodiment, the hub 22 is molded separately from the limiter 26', which is integrated with the extension 96. A difference between the embodiments of FIGS. 6 and 7 compared to that of FIGS. 4 and 5 includes an elongated extension 96 so that the side wall of the extension 96 provides the skin engaging surface 42' of the limiter 26'. In this embodiment, the limiter is supported by the syringe body. By appropriately choosing the dimensions of the needle 24 and the length of the extension 96, the desired distant d between the skin engaging surface 42 and the needle tip 40 can be achieved.

FIG. 7 also illustrates a needle shield 110, which preferably is provided on the hub 22 and needle 24. The needle shield 110 facilitates inserting the hub 22 within the receiver 90 until the hub 22 is appropriately received within the extension 96 so that the intradermal delivery device 80 is ready for use. The needle shield 110 can be discarded after the hub 22 is in position. Alternatively, the needle shield 110 can be replaced over the needle 24 after an injection is complete to avoid the possibility for a needle stick while handling the intradermal delivery device 80 after it has been used. Although the shield 110 is only shown in FIG. 7, it preferably is utilized with the embodiments of FIGS. 4-7.

This invention provides an intradermal needle injector that is adaptable to be used with a variety of syringe types. Therefore, this invention provides the significant advantage of facilitating manufacture and assembly of intradermal needles on a mass production scale in an economical fashion.

Operation and Use

Having described the preferred embodiments of the intradermal delivery device 80 of the present, including the needle assembly 20 and drug container 60, its operation and use is described below.

Use of the delivery device to administer substances such as drugs, vaccines and the like into the intradermal layer is significantly easier than with a traditional syringe and needle. Using a traditional syringe and needle is technique-dependent and requires considerable skill to develop an acceptable skin wheal. In particular, the needle must be carefully guided at a shallow angle under the skin while maintaining correct orientation of the needle bevel. In contrast, with a prefilled intradermal delivery device of the present invention, the user simply presses the device perpendicularly on to the skin and injects the substance. The depth of penetration of the needle is mechanically limited to the intradermal space. In this way, there is no need to orient the needle bevel during injection. Orienting the device, particularly the needle, perpendicularly to the skin, as well as stability while injecting the substance, is facilitated by the design of the device.

Figure 8:
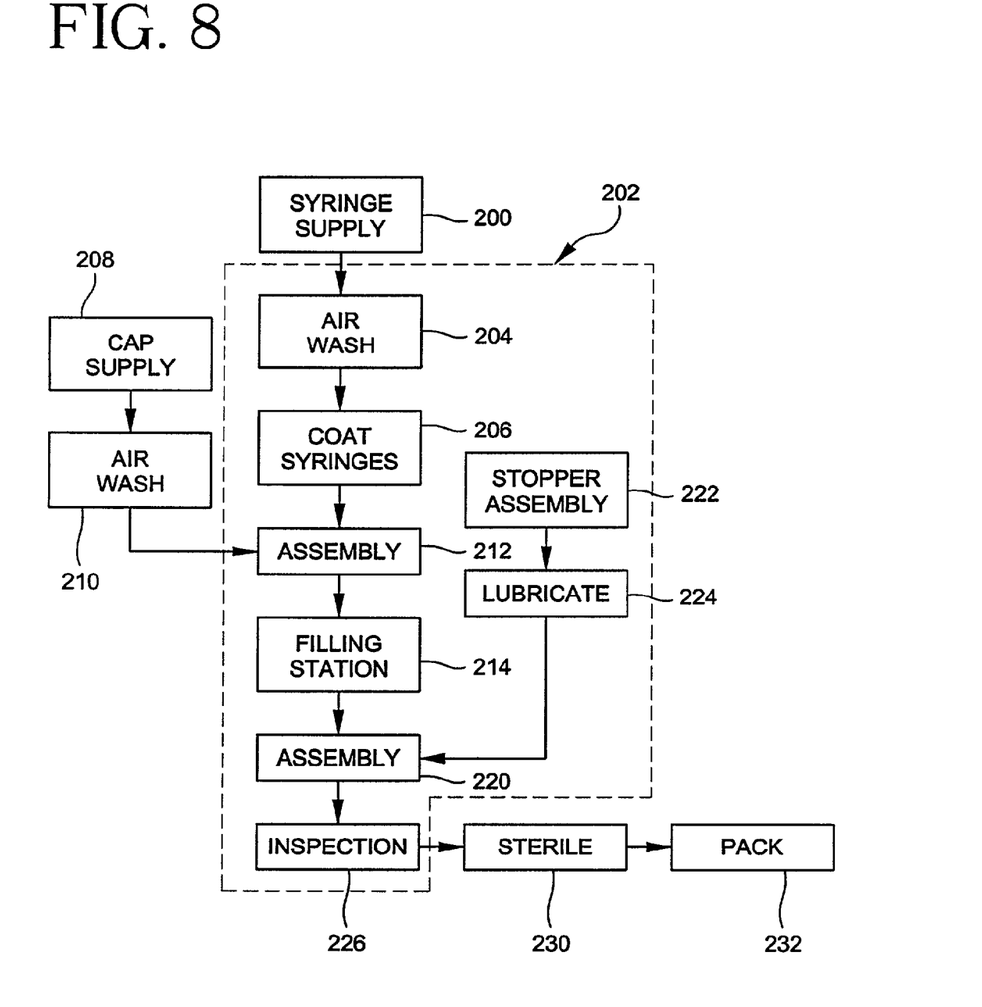
FIG. 8 is a flow chart diagram that schematically illustrates a method of filling a device designed according to this invention.

Referring now to FIG. 8, an example method of filling devices designed according to this invention is schematically illustrated in flow chart format. When the device includes a syringe of the style illustrated in FIG. 3, the following basic procedure is useful for prefilling the syringes with a desired substance.

A supply of syringe barrels 200 includes the desired form of syringe, such as those illustrated and discussed above. A locally controlled environment 202 preferably is maintained in a known manner. The locally controlled environment 202 preferably is situated to immediately accept the syringes without requiring any intermediate cleaning or sterilizing steps between the supply 200 and the environment 202.

In one example, the syringe barrels are washed with air at 204 to remove any particulates from the syringes. The syringes preferably are then coated at 206 with a lubricant such as a lubricating silicone oil on the inner surface. The lubricant facilitates moving the stopper 70 and plunger rod 66 through the syringe during actual use of the device.

The end of syringes that eventually will needle assembly 20 may be capped with a tip cap within the environment 202. In one example, tip caps are supplied at 208. The tip caps are air washed at 210. The cleaned tip caps and syringe barrels are conveyed to an assembly device 212 where the tip caps are secured onto the syringes. The syringe barrel assemblies are then conveyed to a filling station 214 to be filled with the desired substance.

Once filled as desired, the stoppers 70 are inserted into the open end of the syringes at 220. Prior to inserting the stoppers 70, they preferably are assembled with the plunger rods 66 at 222 and lubricated at 224 with a conventional lubricant in a known manner. The assembled, filled syringes preferably are inspected at 226 for defects and discharged from the locally controlled environment.

The syringes typically will be sterilized at 230 and packaged at 232 into individual packages or into bulk packaging depending on the needs of a particular situation. Suitable sterilization techniques are known and will be chosen by those skilled in the art depending on the needs of a particular situation or to accommodate the properties of a given substance. Sterilizing a device designed according to this invention can be completed before or after packaging.

Variations of the filling steps are within the scope of this invention. For example, the stopper can be inserted first, then fill the syringe, followed by applying a tip cap. Additionally, when the device includes a syringe body of the type shown in FIGS. 4 and 5, for example, the filling operation obviously does not include insertion of a stopper nor the lubrication steps described above. Instead, appropriate filling techniques that are known are utilized.

The actual insertion of the desired substance into the syringe body can be accomplished in any of several known manners. Example filling techniques are disclosed in U.S. Pat. No. 5,620,425 to Hefferman et al.; U.S. Pat. No. 5,597,530 to Smith et al.; U.S. Pat. No. 5,537,042 to DeHaen; U.S. Pat. No. 5,531,255 to Vacca; U.S. Pat. No. 5,519,984 to Veussink et al.; U.S. Pat. No. 5,373,684 to Veussink et al.; U.S. Pat. No. 5,265,154 to Liebert et al.; U.S. Pat. No. 5,287,983 to Liebert et al.; and U.S. Pat. No. 4,718,463 to Jurgens, Jr. et al., each of which is incorporated by reference into this specification.

The description given above provides example implementations of this invention. Variations and modifications may become apparent to those skilled in the art that do not necessarily depart from the basis of this invention. The scope of legal protection given to this invention can only be determined by studying the following claims.

What is claimed is:

1. An intradermal delivery device for use in making intradermal injections, comprising:
   a drug container formed of two sheets of thermoplastic material including a body portion that is generally flat and surrounds a reservoir adapted to contain a selected substance and an outlet port that allows the substance to exit the reservoir during an injection;
   a needle having a fixed length, wherein said fixed length is selected to be suitable for handling during manufacture of said intradermal delivery device, the needle having a forward end that is adapted to penetrate the skin of an animal;

a limiter that is substantially located at a distal end of the needle, wherein said limiter surrounds the needle and is fixed with respect to said outlet port and has a skin engaging surface that is adapted to be placed against the skin of the animal to receive an intradermal injection, the needle forward end extending away from the skin engaging surface a preselected distance from 0.5 mm to 3.0 mm which is set during manufacture of the intradermal delivery device such that the limiter limits an amount that the needle forward end penetrates the skin which is equivalent to the preselected distance and wherein the preselected distance is substantially less than the needle fixed length;

a receiver secured to the outlet port of the drug container, the receiver comprising a flange that rests against the body portion of the drug container, an extension that extends away from the flange in a direction opposite from the outlet port, wherein the needle is received within the extension, wherein the receiver supports a sealing membrane that closes the outlet port, a hub portion that supports the needle and is secured at a first end via a snap fit arrangement within the extension of the receiver, wherein an opposite end of the hub portion includes a plurality of extensions that are nestingly received against abutment surfaces within the limiter, wherein the hub portion and the limiter are integrally molded as a single piece of plastic material, wherein the needle penetrates the sealing membrane when the hub portion is received within the extension of the receiver, wherein the skin engaging surface surrounds the needle and has a thickness defined between an inner diameter and an outer diameter, and wherein the inner diameter is at least five times greater than an outside diameter of the needle, wherein limiter comprises a plurality of ribs, and wherein the plurality of ribs are provided on an outer surface of the limiter and extend radially therefrom a greater distance than a remainder of the outer surface of the limiter.

2. The device of claim 1, wherein the skin engaging surface is generally flat and extends through a plane that is generally perpendicular to an axis of the needle.

3. The device of claim 1, wherein the skin engaging surface is continuous.

4. The device of claim 1, wherein the skin engaging surface includes a contact surface area that is large enough to stabilize the assembly in a desired orientation relative to the skin.

5. The device of claim 1, wherein the plurality of ribs extend beyond the skin engaging surface.

6. The device of claim 1, wherein the skin engaging surface is concave.

7. The device of claim 1, wherein the plurality of ribs does not extend beyond the skin engaging surface.

8. The device of claim 1, wherein the plurality of ribs provides structural integrity and facilitates handling of the intradermal delivery device.

9. An intradermal delivery device for use in making intradermal injections, comprising:

a drug container formed of two sheets of thermoplastic material including a body portion that is generally flat and surrounds a reservoir adapted to contain a selected substance and an outlet port that allows the substance to exit the reservoir during an injection;

a needle having a fixed length, wherein said fixed length is selected to be suitable for handling during manufacture of said intradermal delivery device, the needle having a forward end that is adapted to penetrate the skin of an animal;

a receiver secured to the outlet port of the drug container, the receiver comprising a flange that rests against the body portion of the drug container, an extension that extends away from the flange in a direction opposite from the outlet port, wherein the needle is received within the extension, wherein the receiver supports a sealing membrane that closes the outlet port;

a hub portion that supports the needle and is secured at a first end via a snap fit arrangement within the extension of the receiver, wherein the needle penetrates the sealing membrane when the hub portion is received within the extension of the receiver, wherein the extension of the receiver provides a limiter that is substantially located at a distal end of the needle, wherein said limiter surrounds the needle and is fixed with respect to said outlet port and has a skin engaging surface that is adapted to be placed against the skin of the animal to receive an intradermal injection, the needle forward end extending away from the skin engaging surface a preselected distance from 0.5 mm to 3.0 mm which is set during manufacture of the intradermal delivery device such that the limiter limits an amount that the needle forward end penetrates the skin which is equivalent to the preselected distance and wherein the preselected distance is substantially less than the needle fixed length.

10. The device of claim 9, further comprising a needle shield removably provided on the hub portion and the needle, wherein the needle shield is configured to insert the hub portion and the needle within the receiver until the hub portion is received within the extension.

* * * * *